United States Patent [19]

Roberts et al.

[11] Patent Number: 5,538,899

[45] Date of Patent: Jul. 23, 1996

[54] ANALYZING FOR ALKYL KETENE DIMERS

[75] Inventors: John C. Roberts, Broadbottom; Ya J. Zhou, Manchester, both of United Kingdom

[73] Assignee: The University of Manchester Institute of Science and Technology, United Kingdom

[21] Appl. No.: 211,475

[22] PCT Filed: Oct. 5, 1992

[86] PCT No.: PCT/GB92/01821

§ 371 Date: Aug. 2, 1994

§ 102(e) Date: Aug. 2, 1994

[87] PCT Pub. No.: WO93/07484

PCT Pub. Date: Apr. 15, 1993

[30] Foreign Application Priority Data

Oct. 4, 1991 [GB] United Kingdom ............... 9121118

[51] Int. Cl.$^6$ .................................................. G01N 31/22
[52] U.S. Cl. ..................... 436/128; 436/127; 436/130; 436/166
[58] Field of Search .............. 436/14, 128, 127, 436/130, 166, 164; 422/82.05, 82.09, 166

[56] References Cited

FOREIGN PATENT DOCUMENTS 280156  8/1988  European Pat. Off. .
1695108 4/1971  Germany .

OTHER PUBLICATIONS

G. Stöckelmann et al. Chem. Ber. 1969, 102, 455–458.
N. V. Stepanyuk et al. Chem. Abstr. 1966, 65, 4522g.
J. A. Berson et al, J. Am. Chem. Soc. 1956, 78, 1625–1631.
G. A. Taylor J. Chem. Soc. 1965, 3332–3335.
R. Adam et al. J. Am. Chem. Soc. 1952, 74, 5491–5497.
T. Kato et al. Chem. Pharm. Bull. 1972, 20, 133–141.
T. Kato et al. Chem. Pharm. Bull. 1972, 20, 142–146.
Wilson et al. J. Org. Chem., (1984) 49(4) 722–725 (Abstract Only).
Nudelman et al., Synthesis, (1989) (5) 387–389.
Kato, Chem Pharm. Bull. 28(7) 2129–2135 (1980).
Fresenius Zeitschrift Fur Analytische Chemie vol. 323, No. 5, 1986, Berlin De, pp. 487–489, M. Kapernaum et al. Spectrometric Detection and Determinationof Ketene.

*Primary Examiner*—Jill Warden
*Assistant Examiner*—Arlen Soderquist
*Attorney, Agent, or Firm*—Clifford W. Browning; Woodard, Emhardt, Naughton, Moriarty & McNett

[57] ABSTRACT

A method of analysing a sample for alkyl ketene dimer (AKD) comprises treating the sample (or extract thereof) with a reagent which will react with an AKD to produce a detectable derivative. The preferred reagent is 4-(N,N'-dimethylamino)pyridine.

10 Claims, 5 Drawing Sheets

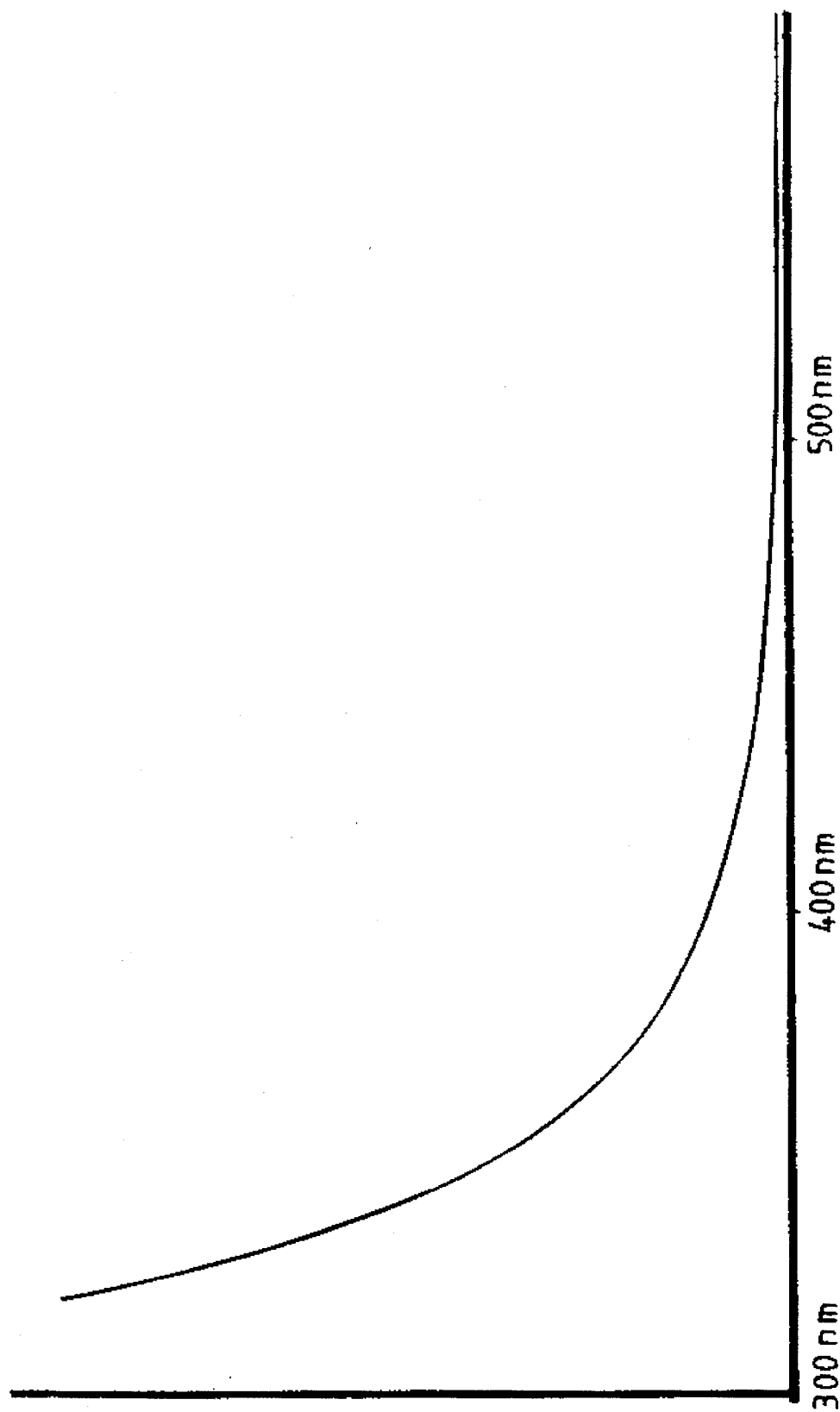

ANALYZING FOR ALKYL KETENE DIMERS

BACKGROUND OF THE INVENTION

The present invention relates to a method of analysing for an alkyl ketene dimer.

Alkyl ketene dimers are higher analogues of diketene and are of the formula

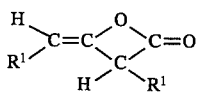

where each $R^1$ represents the same or different alkyl group (usually a long chain alkyl group, e.g. $C_{14}$–$C_{18}$). Generally the alkyl group is a linear, straight chain group.

Alkyl ketene dimers (AKD) are used in the sizing of paper, for which they are preferred to rosin sizes for certain applications. For a number of applications, it may be desired to analyse for the AKD either qualitatively or quantitatively, e.g. on the sized paper or in the water drained through the wire of a Fourdrinier machine. The most common technique used for the study of AKD sizing is by radioactive tracers. Although this technique permits an accurate determination of AKD size retention in paper, it is limited to use in specialised laboratories. IR and HPLC have been tried for analysis of AKD but they are quite complex and not particularly convenient.

It is therefore an object of the present invention to provide a method of analysing for an alkyl ketene dimer which obviates or mitigates the abovementioned disadvantages.

SUMMARY OF THE INVENTION

According to the present invention there is provided a method of analysing a sample for an alkyl ketene dimer (AKD) comprising treating the sample or extract thereof with a compound having a nitrogen-containing heterocyclic ring, said compound having at least one amino substituent on the ring containing the nitrogen atom, to produce a detectable derivative, and effecting a detection for said derivative.

For preference the derivative is one which absorbs in the visible and/or ultra-violet region of the spectrum. In the case where the derivative is coloured, the appearance of a colour change (upon reaction of the sample or extract with the reagent) demonstrates the presence of AKD in the original sample. Alternatively or additionally the amount of the derivative may be determined spectroscopically so as to provide a quantitative analysis of the amount of AKD present in the original sample.

The heterocyclic ring may optionally be further substituted and may be part of a fused ring system. Preferably the heterocyclic ring is a 6-membered ring and preferably also the amino substituent is an N-alkylamino or N,N-dialkylamino substituent, most preferably having 1 to 4 carbon atoms. The preferred compounds are those having a pyridine ring, most preferably with the amino substituent at the 4-position.

The preferred reagent for use in the invention is of the general formula

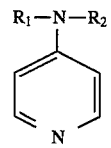

in which $R_1$ and $R_2$ are the same or different $C_1$–$C_4$ alkyl groups. The heterocyclic ring may include other substituents.

Most preferably the reagent is 4-(N,N-dimethylamino)pyridine (DMAP) which we have found to react with AKD to produce a yellow derivative. Whilst we do not wish to be bound by any theory, we believe that the reaction between the AKD and DMP produces a yellow derivative of the following structure:

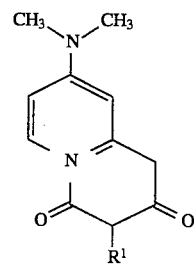

We have established that the reaction between AKD and DMAP proceeds quantitatively, and this allows determination of AKD (in the original sample) by visible an/or ultraviolet spectroscopy. In particular, the yellow reaction product of AKD with DMAP has been found to display two absorbance maxima at 450 nm (visible range) and 338 nm (UV range), either of which can be used for the determination of AKD.

The method of the invention may be used for the analysis of AKD in "waste" water from the paper making process, in the "input" water to the process, or on the paper itself. We have established that DMP reacts specifically with AKD and not with hydrolysis products thereof nor with AKD which has reacted with cellulose. The method may also be used to analyse AKD emulsions to test for the extent (if any) to which the AKD has been hydrolysed.

In practising the method of the invention the DMAP (or other reagent, e.g. another amino substituted nitrogen containing heterocycle) should be dissolved in an organic solvent which has the ability to dissolve not only the reagent but also AKD and the product of their reaction. Suitable solvents are generally non-polar organic solvents (particularly those without significant absorption at the wavelengths at which the AKD/DMAP derivative absorbs. Chloroform is the preferred solvent.

For qualitative determinations, the DMAP solution and sample possibly containing AKD (or extract thereof) may simply be mixed together in which case the appearance of a colour change confirms the presence of AKD. For quantitative work, the mixture of sample (or extract) and DMAP solution are preferably heated together, e.g. by refluxing at the solvent boiling point for up to 2 hours. We have established that the time required for the reagent/AKD reaction to go to completion is dependent on the DMAP concentration and the heating temperature. The fact that the reaction has reached completion may be detected by periodically measuring the absorbance of the reaction mixture (at one or other absorbance maximum) until no further change is detected. The amount of AKD/DMAP derivative in the product mixture may then be determined by standard spectroscopic methods (e.g. based on the Beer-Lambert Law).

Typically the initial concentration of DMAP in the organic solvent will be 25–100 mg/liter, preferably 40–80 mg/liter.

To detect the presence of unreacted AKD on paper, a sample of the paper may firstly be extracted with one of the aforementioned solvents and the extract then reacted with DMAP as outlined above.

If it is desired to detect AKD in, for example, the "input" or "waste" water, then the DMAP solution may either be added directly to the aqueous sample or an organic solvent extract thereof.

To analyse an AKD emulsion, (e.g. for extent of hydrolysis), the emulsion may be freeze dried. AKD and other soluble organic chemicals may then be extracted with an organic solvent and reacted with DMAP as above.

A further possible application of the method is in the detection of unreacted AKD on paper by treating an area of the paper with DMAP and then using an optical probe to detect the presence of any colouration at the wavelength at which the AKD/DMAP derivative absorbs.

BRIEF DESCRIPTION OF THE DRAWING FIGURES

The invention will be further described by way of example only with reference to the accompanying drawings, in which:

FIG. 5 is a uv/visible spectrum of extracts of paper.

DETAILED DESCRIPTION OF THE PREFERRED EMBODIMENT

Figure 1:
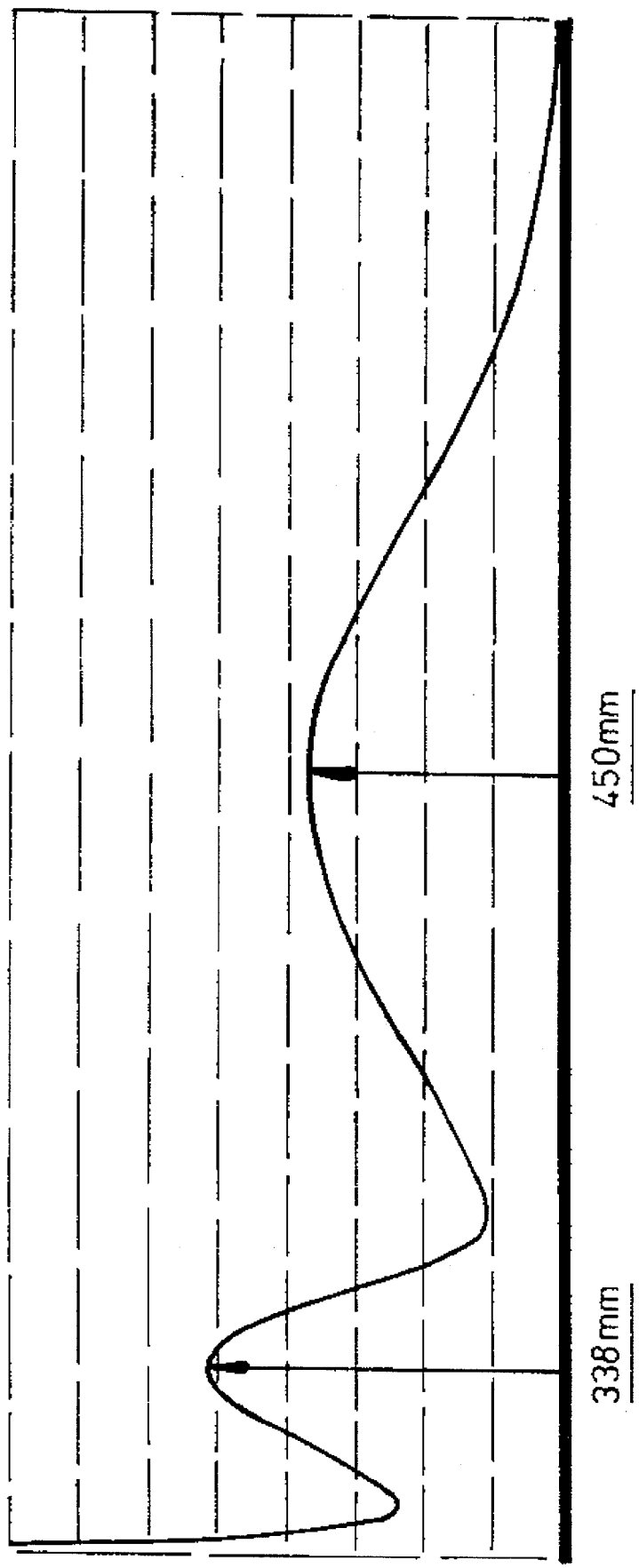
FIG. 1 is the uv/visible spectrum of the coloured complex of TDKD with DMAP.

To demonstrate the reaction between TDKD (tetradecyl ketene dimer) and DMAP, the TDKD was mixed with an excess of DMAP in chloroform. The mixture was then refluxed at the boiling point of chloroform for one hour. The colour of the solution became yellow. After cooling, the yellow solution was analysed on a visible/ultraviolet spectrophotometer. The spectrum obtained in shown in FIG. 1. It will be noted that the spectrum displays two absorbance maxima, i.e. at 338 nm and 450 nm. The peak at 338 nm is the sharper of the two and can be used for more sensitive determination, especially at low concentrations.

The influence of heating time on the reaction was determined by the following procedure, 0.01 g of TDKD was dissolved in about 25 ml of chloroform and the solution was then made up to 100 ml in a volumetric flask. 1 g of DMAP was dissolved in 100 ml of chloroform. Four 25 ml distillation flasks were washed and dried in an oven. 10 ml of TDKD solution and 8 ml of the DMAP solution were pipetted into each flask (i.e. a DMAP:TDKD ratio of 80:1). The mixtures were refluxed for different periods of time (30, 45, 60, 120 minutes). After cooling, the solutions were separately made up to 25 ml in volumetric flasks. The concentration of TDKD was 40 mg/l.

The rate of the reaction between DMAP and TDKD was monitored by measuring the absorbance peaks at 338 nm and 450 nm. Although the reaction was quite fast at first, it was found that time and heat were necessary to complete the reaction. The amount of DMAP added was also found to affect the rate of reaction.

Figure 2:
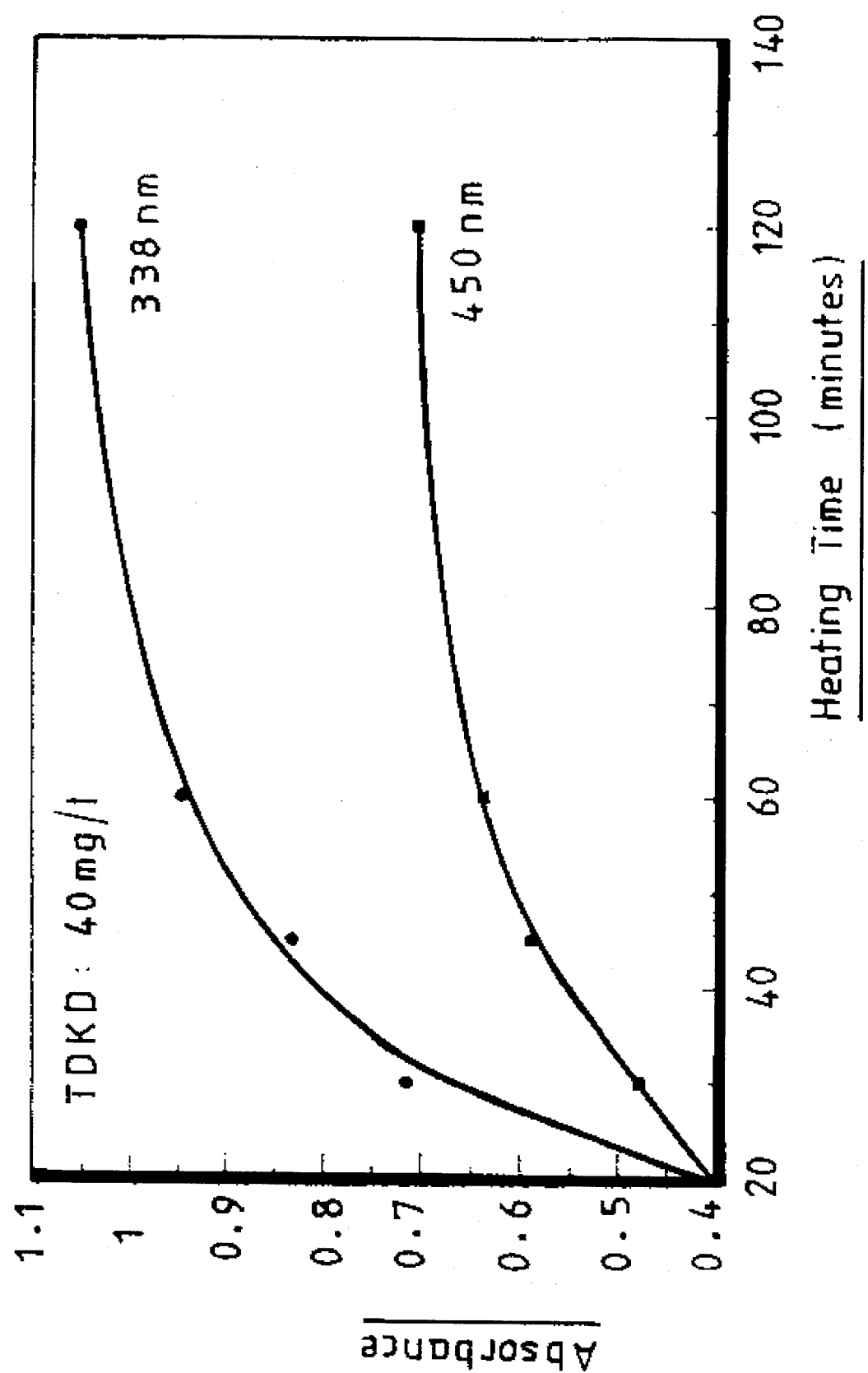
FIG. 2 illustrates the influence of heating time on the DMAP/TDKD reaction.

FIG. 2 shows absorbance at 450 nm and 338 nm as a function of heating time. It can be seen that the reaction went to completion after about 120 minutes of refluxing at the solvent boiling point. It was also noticed that the concentration of TDKD affected the reaction. The refluxing time can be reduced at high concentrations.

Experiments were also conducted to determine the addition ratio of TDKD and DMAP on the reaction. 0.01 g of TDKD was dissolved in chloroform and made up to 100 ml. Each 10 ml of the solution was then pipetted into four 25 ml distillation flasks. The DMAP solution was prepared as above, and 2, 4, 7 and 10 ml of the solution were separately pipetted into the flasks. TDKD and DMAP were mixed in chloroform at different ratios (TDKD/DMAP: 1/20, 1/40, 1/70, 1/100 by weight). The mixtures were refluxed for 90 minutes. After cooling, the solutions were separately made up to 25 ml. The measurements were then carried out on a v/uv spectrophotometer.

Figure 3:
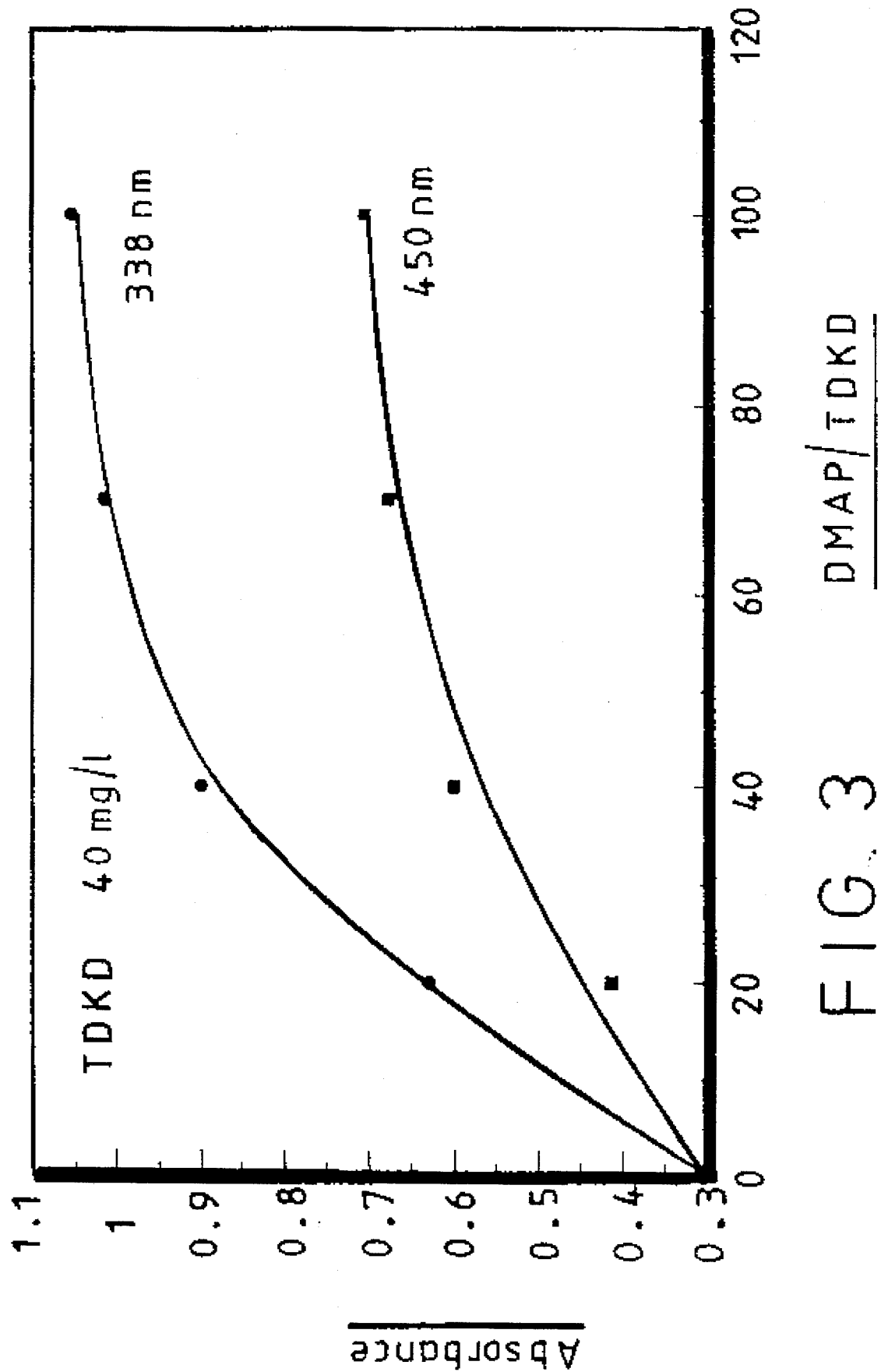
FIG. 3 illustrates the influence of addition ratio of DMAP and TDKD on the reaction.

FIG. 3 shows the rate of the reaction at different ratios of addition of TDKD and DMAP (1.5 hours refluxing). An increase in the addition level of DMAP clearly promotes the reaction. DMAP probably acts both as a reactant and as a base catalyst. It was also found that a very large excess of DMAP affected the stability of colour. Usually, the ratio should be maintained between 70 and 100 to 1.

For the quantitative application of the method of the invention, a calibration curve was generated as follows.

Figure 4:
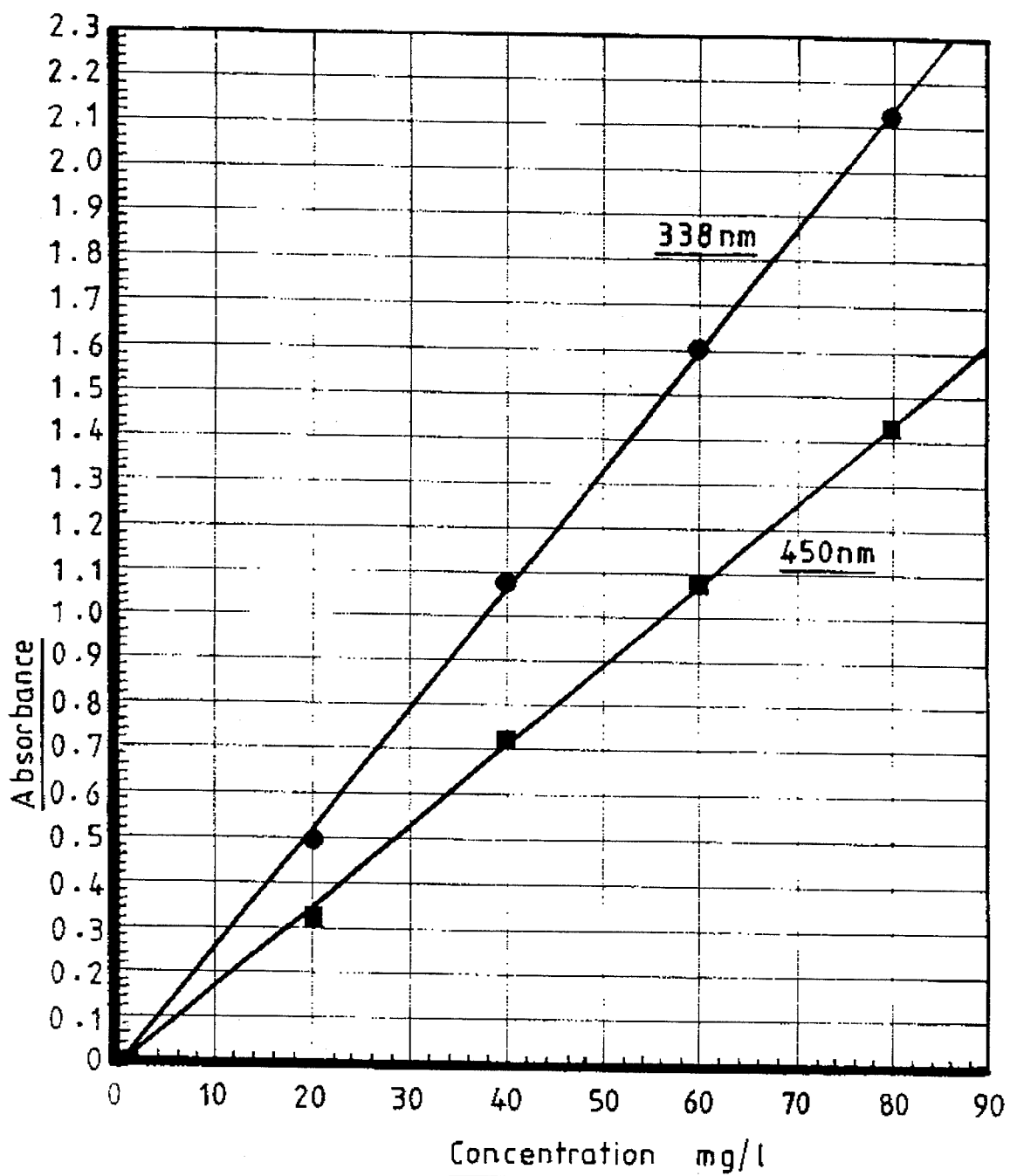
FIG. 4 is a calibration curve for the determination of TDKD at 338 nm and 450 nm.

0.01 g of TDKD was dissolved in chloroform and made up to 100 ml. 5, 10, 15, 20 ml of the solution were then separately pipetted into four 25 ml distillation flasks. DMAP solution was prepared as above. 4, 8, 12 and 16 ml of the solution were separately added to the flasks. TDKD and DMAP were mixed at a ratio of 1/80. The mixtures were then refluxed for two hours. After cooling, the solutions were separately made up to 25 ml. Absorbances at 338 nm and 450 nm were then measured on a v/uv spectrophotometer. The results are shown in FIG. 4.

It can be seen that the concentration is linearly related to absorbance in accord with the Beer-Lambert law. From the calibration curves, two equations were deduced:

$$A = 0.0181 \times C + 0.012 \quad (4.2) \text{ at } 450 \text{ nm}$$

$$A = 0.0268 \times C + 0.012 \quad (4.3) \text{ at } 338 \text{ nm}$$

where:
A=absorbance at 450 nm or 338 nm
C=concentration of TDKD (mg/l)

For an unknown sample of TDKD, its concentration can then be determined from the equations or from the calibration curves.

One sample of commercial AKD (Aquapel C94) was freeze-dried. AKD and other soluble organic chemicals were extracted from the cationic starch matrix with chloroform. An excess of DMAP was then added to the extracts. The mixture was refluxed for 1 hour and analyzed on a v/uv spectrophotometer.

Although this commercial AKD is a mixture of different alkyl ketene dimers, the v/uv spectrum shows only two absorbance peaks which are at the same wavelength as those obtained using pure TDKD. This indicates that the functional group of AKD which affects the colour is the lactone ring. The difference in alkyl chains does not have any influence on the absorption maxima of the colour reaction. Therefore, in practice, one particular AKD could be taken as a standard and the total amount of different kinds of AKDs in the solution then calculated from the standard.

Extracts from paper with a solvent usually shows a significant absorbance even without the addition of DMAP. This is particularly true for paper which has turned yellow during ageing. FIG. 5 shows the v/uv spectrum of chloroform extracts (no addition of DMAP) of paper made from a bleached Kajaani sulphite pulp sized with Aquapel C94 (0.2%). At a wavelength of 450 nm, the absorbance is small and can be neglected. However, it shows quite a high absorbance at 338 nm. Hence the influence of extracts of paper should be taken into account at a wavelength of 338 nm. Usually pure chloroform can be used as a reference at a wavelength of 450 nm. However, it is better to use a blank extract as a reference instead of pure chloroform when measurements are made at 338 nm.

Fines from paper during extraction were also found to interfere with the absorbance, especially for paper made from highly beaten pulp and at high addition levels of filler. Fines should therefore be removed before measurement.

The invention is illustrated by the following non-limiting example.

EXAMPLE (i) Preparation of Paper Samples:

A bleached sulphite pulp (pH7–8) was used to make paper on the UMIST pilot paper machine. Aquapel C94 (0.2%, based on bone-dry fibre) was added to the pulp at the mixing box. The drier section was adjusted to a constant temperature (70° C., 90° C. or 110° C.) and the paper stored in a humidity and temperature-controlled laboratory (23° C., 50% RH). Basis weight: 60 g/m².

Sizing was measured on a Hercules Sizing Tester (10% formic acid ink, the reflectance end point: 80%).

(ii) Analysis of Paper Samples.

(a) Paper samples produced at each of the three drier section temperatures (i.e. 70° C., 90° C. and 110° C.) were analysed at various intervals. The samples were extracted with chloroform in a Soxhlet extractor for eighteen hours. The extract containing unreacted AKD was analysed quantitatively using DMAP in accordance with the method of the invention.

(b) Additionally retention of the AKD on the as produced paper was determined by taking samples from the wire section, freeze drying, extracting with chloroform and analysing for AKD by the above method. The retention of AKD in the sheet before drying was found to be 1.61 mg/g as measured by visible and ultraviolet spectroscopy.

The results for (a) are shown in Table 2.

TABLE 2

The effect of drying temperature and storage time on the degree of sizing (HST) and the amount of unreacted AKD (Aquapel C94)

| Storage time | 70° C. Unreacted AKD (mg/g) | 70° C. HST values (seconds) | 90° C. Unreacted AKD (mg/g) | 90° C. HST values (seconds) | 110° C. Unreacted AKD (mg/g) | 110° C. HST values (seconds) |
|---|---|---|---|---|---|---|
| 2 hours | 1.42 | 21.9 | 1.06 | 77.7 | \ | 168.2 |
| 1 days | 1.20 | 83.1 | 1.23 | 128.4 | 1.08 | 211.4 |
| 3 days | 0.87 | 93.9 | 0.93 | 170.5 | 0.65 | 238.0 |
| 7 days | 0.83 | 126.7 | 0.46 | 170.9 | 0.38 | 240.6 |
| 14 days | 0.47 | 128.5 | 0.28 | 255.1 | 0.24 | 291.2 |
| 21 days | 0.33 | 133.9 | 0.11 | 221.4 | 0.07 | 278.6 |
| 28 days | 0.23 | 156.7 | 0.07 | 214.0 | 0.06 | 279.3 |

Note:
The retention of AKD in the sheet before drying was 1.61 mg/g as measured by visible and ultraviolet spectroscopy As may be seen from Table 2, the method of the present invention may be used for following the reaction of AKD with paper. In other words, the amount of AKD on the paper can be seen to decrease with time as sizing develops.

We claim:

1. A method of analysing a sample for an alkyl ketene dimer (AKD) comprising treating the sample or extract thereof with a reagent having a nitrogen-containing heterocyclic ring, said reagent having at least one N-alkylamino or $N,N^1$-dialkylamino substituent, wherein the alkyl group or alkyl groups have 1–4 carbon atoms, on the ring containing the nitrogen atom, to produce a detectable derivative, and effecting a detection for said derivative by spectroscopy.

2. A method as claimed in claim 1 wherein the reagent is one yielding a derivative which absorbs in the visible and/or ultraviolet region of the spectrum.

3. A method as claimed in claim 1 wherein the heterocyclic ring is a six membered ring.

4. A method as claimed in claim 3 wherein said heterocyclic ring is a pyridine ring.

5. A method as claimed in claim 4 wherein the amino substituent is at the 4-position relative to the nitrogen atom.

6. A method as claimed in claim 5 wherein the reagent is of the general formula

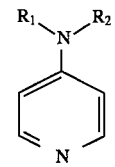

in which $R_1$ and $R_2$ are the same or different $C_1$–$C_4$ alkyl group.

7. A method as claimed in claim 6 wherein $R_1=R_2=CH_3$.

8. A method as claimed in claim 7 wherein the sample and the reagent are heated in a solvent which dissolves the reagent, AKD, and the derivative.

9. A method as claimed in claim 8 wherein the solvent is chloroform.

10. A method as claimed in claim 6 wherein the detection is by a spectroscopic technique effected at or substantially at a wavelength of 338 nm and/or 450 nm.

* * * * *